United States Patent
Worthington

(10) Patent No.: US 7,059,327 B2
(45) Date of Patent: Jun. 13, 2006

(54) TRACHEOSTOMA VALVE

(75) Inventor: Ian David Worthington, West Yorkshire (GB)

(73) Assignee: Kapitex Healthcare Limited, West Yorkshire (GB)

( * ) Notice: Subject to any disclaimer, the term of this patent is extended or adjusted under 35 U.S.C. 154(b) by 0 days.

(21) Appl. No.: 10/502,293

(22) PCT Filed: Jan. 22, 2003

(86) PCT No.: PCT/GB03/00248

§ 371 (c)(1),
(2), (4) Date: Apr. 8, 2005

(87) PCT Pub. No.: WO03/061531

PCT Pub. Date: Jul. 31, 2003

(65) Prior Publication Data

US 2005/0178390 A1    Aug. 18, 2005

(30) Foreign Application Priority Data

Jan. 23, 2002  (GB) ................................ 0201470.2

(51) Int. Cl.
*A61M 16/00* (2006.01)
(52) U.S. Cl. ........................... 128/207.16; 128/207.14; 128/200.26
(58) Field of Classification Search .......... 128/200.26, 128/207.14, 207.17, 207.16; 623/9
See application file for complete search history.

(56) References Cited

U.S. PATENT DOCUMENTS

| 4,040,428 | A | * | 8/1977 | Clifford | 128/207.16 |
| 4,582,058 | A | * | 4/1986 | Depel et al. | 128/207.17 |
| 4,627,433 | A | * | 12/1986 | Lieberman | 128/207.16 |
| 4,809,693 | A | * | 3/1989 | Rangoni et al. | 128/207.16 |
| 5,059,208 | A |   | 10/1991 | Coe et al. | |
| 5,727,594 | A | * | 3/1998 | Choksi | 137/859 |
| 5,738,095 | A |   | 4/1998 | Persson | |
| 6,193,751 | B1 | * | 2/2001 | Singer | 623/9 |
| 6,921,417 | B1 | * | 7/2005 | Persson | 623/9 |

FOREIGN PATENT DOCUMENTS

WO    WO 95/17138 A1    6/1995

* cited by examiner

*Primary Examiner*—Mital Patel
(74) *Attorney, Agent, or Firm*—Sughrue Mion, PLLC

(57) ABSTRACT

A tracheostoma valve is described for use within a tracheostoma to facilitate speech by use of a vocal prosthesis, which consists of a valve housing defining a valve cavity having an airflow passage therethrough between at least one rearward and at least one forward aperture, and a valve member. The valve member includes a fixed rear portion connected to a forward portion by a collapsible sleeve such that the forward portion is deployable from a collapsed configuration under vegetative breathing pressure wherein the air flow passage is open to an expanded configuration under speech pressure whereat the forward portion acts to restrict flow through the air flow passage.

15 Claims, 3 Drawing Sheets

TRACHEOSTOMA VALVE

This is a National Stage of Application No. PCT/GB2003/00248, filed Jan. 22, 2003.

The invention relates to a valve to be connected to a tracheostoma to facilitate speech.

BACKGROUND OF THE INVENTION

Normal human speech makes use of expired air from the lungs flowing up through the trachea and the larynx to vibrate the vocal cords in the larynx. As a result of disease it is sometimes necessary to remove by surgery a portion of the trachea which may include the larynx (laryngectomy).

Since the larynx normally serves also to prevent contamination of the lungs by oesophageal contents, the passage between the trachea and the pharyngeal oesophagus must be blocked. Consequently at laryngectomy an opening, or stoma, is created to the outside of the throat at the base of the patients neck to which the trachea is permanently diverted. In such patients breathing is then through this tracheostoma.

To restore vocal function it becomes necessary to provide alternative sound producing apparatus as a substitute for the vocal cords. For example it is possible during the surgical procedure to open a fistula between oesophagus and trachea allowing the passage of air into the oral cavity and into which a voice prosthesis, for example in the form of a cylindrically shaped, one-way valve is inserted into this tracheo-oesophagal passageway, is fixed. In any event, to restore vocal function in a patient with a tracheostoma it will be necessary for the tracheostoma to be blocked to allow the patient to force air into the area above the stoma and thus induce vibrations to produce the basis for an acceptable and audible voice.

It is necessary therefore that the tracheotomy patient is able to occlude the stoma when speaking. Most simply this can be done by covering the stoma for example by one or more fingers. However, this is not always practical or pleasant, particularly given that the stoma often is coated by secretion and can have an irregular shape.

More preferably, the stoma is occluded by a manually operated valve. This can be. However it is also known to provide tracheostoma valves which operate automatically. These have a movable closure resiliently biased to an open position. In such a device valve closure pressures are such that normal vegetative breathing pressure is insufficient to move the closure to a closed position and the patient may readily inhale and exhale normally. Speech, however, is initiated at somewhat higher pressure levels. The closure is adapted so that these higher pressures move the valve to a closed position, blocking the free discharge of exhaled air out of the stoma. The air can thus be diverted through a voice prosthesis to produce sound that can be shaped into acceptable speech.

Prior art devices typically include a movable closure, such as a movable diaphragm, contained within a cannular portion inserted into the stoma. This is moveable between an open position for normal breathing and a closed position where the stoma is occluded for speech and is biased to the open position for example by a biasing spring. An accelerating flow of air initiates closing of the valve for speech.

Two further refinements are known. First, a further "cough" valve is often provided as a safety feature closed at normal and speaking pressures but whereby very high pressures cause this to open. For example, where the closure member is slideable in a cannulus, this can be provided at the sides thereof. Second, with different patients and changing exertion and respiration levels, no single closure can have the correct mechanical characteristics to work ideally in all situations, and some prior art valves are adjustable, for example by means of a screw thread setting distance between open and closed position and/or the exchanging of interchangeable springs biasing the valve to alter the closure pressure, to allow this to be changed by the patient.

Embodiments of such valves illustrating some or all of these features are disclosed for example in U.S. Pat. Nos. 4,582,058, 5,059,208, 5,738,095, and 6,193,751.

These prior art devices all have complex multi-component mechanisms. This can raise costs, increase the possibility of malfunctions, and in particular make the tracheostoma valves difficult to operate and keep clean. This last point can be a particular problem. The valves can easily become contaminated with mucus from the trachea and/or with dust and like contaminants from outside. This can effect the efficiency not only of the functioning of the valve but also of the general functioning of the stoma itself. This is a particular problem in patients who have had a laryngectomy, since the procedure itself tends to lead to an increase in mucus production.

Furthermore, it is frequently desirable to provide for a filter in the stoma, for example to serve as a means to keep external contaminants out of the trachea, as a means in part to normalise conditions within the trachea, in particular heat-moisture, as a means to control air flow resistance during normal breathing etc, to protect the stoma, or simply for cosmetic purposes. Not all prior art devices are compatible for use with such prior art stoma filters, such as heat-moisture exchange (HME) filters.

BRIEF SUMMARY OF THE INVENTION

It is an object of the present invention to provide a tracheostoma valve which facilitates speech in laryngectomy patients by remaining open under the pressure of normal vegetative breathing but closing under the pressure associated with speech.

It is a further object of the present invention to provide a tracheostoma valve which is of mechanically simple construction, in particular to permit ease of operation by a user and/or ready cleaning and/or to reduce costs to such an extent that the valve or components thereof are disposable and replaceable.

It is a particular object of the present invention to provide a tracheostoma valve having an operating valve air pressure which is stably but adjustably settable by a patient in simple manner.

Thus, according to the invention in its broadest concept, there is provided a tracheostoma valve including a valve housing defining a valve cavity and having at least one rearward and at least one forward aperture such as to define an air flow passage through the said valve cavity between the rearward and forward apertures; and further comprising within the valve cavity a valve member deployable from a first collapsed configuration under vegetative breathing pressure wherein the said air flow passage is open to a second expanded configuration under speech pressure whereat the valve member acts to restrict flow through and in particular substantially or entirely occlude said air flow passage.

DETAILED DESCRIPTION OF THE INVENTION

Figure 1:
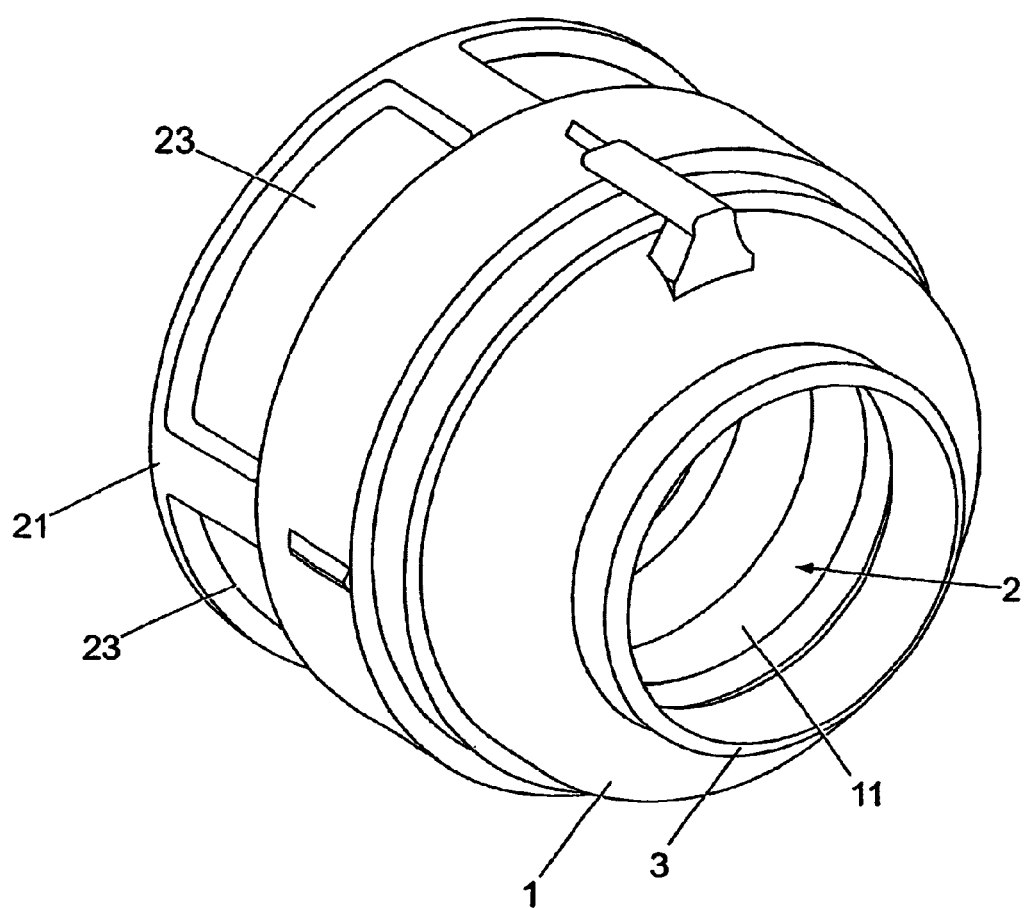
FIG. 1 is a perspective view of an embodiment of the invention looking from the rear.

The invention is characterised in that the valve member comprises a rear portion fixedly mounted to an inner surface of the valve housing rearward of the forward aperture so as to surroundingly and sealingly engage over the rearward aperture, a forward portion, and a collapsibly expandable sleeve portion provided therebetween to surroundingly define a part of the air flow passage, such that the forward portion is deployable from a position in the unexpanded configuration whereat the air flow passage is open to a position in the expanded configuration whereat the forward portion acts to restrict air flow through the air flow passage.

In use air passes during normal vegetative exhalation first through the rear aperture in the rear wall of the valve housing then into the valve cavity, then out through an aperture or apertures within the forward portion (i.e. the side wall portion or forward wall) of the valve housing. During inhalation the air passage route is reversed. Under speech pressure, the exhaled air passage route is restricted, and preferably occluded by the valve member, and at least some and preferably most or all of the air is diverted to an alternative path, passing instead up the trachea beyond the stoma and into the pharyngeal region where speech is facilitated, for example by provision of suitable prior art voice prosthesis, in the familiar manner.

The tracheostoma valve is thus fully automated, closing automatically under breathing pressure and not requiring any action by the user. In accordance with the invention the valve member does not deflect or distort as in some prior art examples, but expands from a collapsed state where an air flow passage between the rearward and forward apertures via the valve member is open to an expanded state where the passage is occluded.

The sleeve portion of the valve member is preferably structured to facilitate expansion of the valve member during use, and in a preferred embodiment has a concertina structure. Thus, the valve serves in effect as a bellows member.

The sleeve portion facilitates transition to the expanded configuration, is collapsibly expandable, and is preferably resiliently biased to the unexpanded, collapsed configuration. This may be achieved by separate biasing means but is preferably achieved in that the sleeve is fabricated from inherently expandable material, such as elastomeric material, and is so configured that the inherent elasticity thus in effect inherently biases the valve member to the unexpanded configuration.

The valve member is thus preferably so constructed as to be biased into the unexpanded, collapsed state when unstressed and under normal vegetative pressure, but to be caused to expand under increased air pressure such that, at air pressure in use such as might be associated with speaking pressure it serves to restrict and in the preferred case close the air passage through the valve cavity.

A valve in accordance with the invention may be of very simple construction. The valve housing may be fabricated from one or a few pieces of relatively rigid material, for example as a rigid plastics moulding. The valve member, or at least the sleeve portion thereof, is preferably flexibly resilient, being either of inherently flexibly resilient material or of a resilient construction or some combination thereof. The valve member is preferably fabricated as a one piece construction from flexibly resilient material and in particular elastomeric material, and is so fabricated to sit in the unexpanded configuration when unstressed.

In this preferred embodiment the inherent flexible resilience thus in effect inherently biases the valve member to the unexpanded configuration, but the structure of the valve member is such that the action of increased air pressure in use such as might be associated with speaking pressure causes it to transform to its expanded configuration whereat it serves to restrict and in the preferred case close the air passage through the valve cavity. This is a very simple construction. Separate closures and springs are not required. There is little mechanically to malfunction, and the valve is likely to be cost-effective to fabricate and easy to use.

For convenience of description of the relationship of various components of the valve to each other, reference is made herein to forward and rearward surfaces and forward and rearward directions by reference to the orientation of the device in use worn by a patient. Thus, references to the rear are references to those parts of the device which will in use sit most closely to the patient's neck, and references to the front are references to those parts of the device which will in use sit most forwardly of the patient's neck. The language used is for convenience only to indicate relative positions of the components of the device, and should not be considered in any way further limiting.

In a typical construction the valve housing comprises a rear wall including a rear aperture and a forward portion comprising a forward wall and a side wall extending between said forward and rear walls, these together defining the valve cavity, the forward portion being provided with a forward aperture such as to define an air flow passage through the said valve cavity between the rearward and forward apertures; and the valve member is deployable from a first collapsed configuration to a second expanded configuration whereat the valve member acts to restrict flow through and in particular substantially or entirely occlude the forward aperture.

References to rear, forward and side wall portions may be construed accordingly, but are intended for convenience only and should not be read as limiting either on the precise shape of or the number of components making up the valve housing. The valve housing and/or each so-called portion may be integrally formed as a single piece construction or may be formed as a multiple component system.

In accordance with the invention the valve member comprises a rear portion fixedly mounted to an inner surface of the valve housing and a forward portion linked by a sleeve portion which serves also to define a part of the air flow passage, whereby the forward portion is adapted to move from a position in the unexpanded configuration whereat the air flow passage is open to a position in the expanded configuration whereat the forward portion acts to restrict air flow through the forward aperture, in particular by at least partly occluding the air flow passage through the sleeve and out of the forward aperture.

The rear portion is fixedly mounted to an inner surface of the valve housing so as to surroundingly and sealingly engage over the rear aperture. The forward portion conveniently incorporates a valve aperture. The sleeve portion surroundingly define a part of the air flow passageway. In use air flows via the rear aperture, through the sleeve, via the valve member aperture, through the main part of the valve cavity and via the forward aperture therein and thence through the forward aperture in the valve housing. It will be apparent that the engagement of the rear portion over the rear aperture, and the walls of the sleeve portion, should both be such as to limit air leakage so that air flows generally through the desired pathway described. Ideally the engagement of the rear portion over the rear aperture, and the walls of the sleeve portion, should both be generally airtight.

The valve member is configured such that on its expansion under speaking pressure this passageway is occluded. The sleeve member is expandable from the collapsed to the expanded configuration to effect this. In a particular preferred configuration the valve member comprises a forward portion incorporating a valve aperture and a substantially airtight sleeve portion therebetween, and a valve seating surface is provided within the valve cavity on an inner surface of the valve housing such that when the valve member is so expanded the forward portion of the valve member seats against the valve seating surface in sealing manner to effect closure of the valve aperture therein and hence generally occlude the air flow passage.

In the preferred embodiment the forward portion of the valve is apertured and the housing is configured to provide a valve seat portion whereat the valve aperture is substantially occluded when the valve portion is in the expanded configuration. In a particularly preferred construction, the forward portion of the valve member comprises a partly apertured forward surface which forward surface is adapted to engage in fluid tight manner with a valve seat surface provided internally on the forward wall of the valve housing to effect closure when the valve member is in the expanded configuration.

The unapertured portion of the forward wall of the valve member then effectively serves as a pressure surface responsive to breathing pressure to effect expansion of the sleeve portion as breathing pressure increases. The valve member under normal vegetative pressures is resiliently biased by the resilience of the sleeve portion into an unexpanded configuration. The action of increased breathing pressure for speech on the pressure surface so provided acts against this inherent resilience and causes the valve member to expand until it seats against the valve seat wall in airtight manner to close the air passage through the valve. In this way it can again be emphasised that the valve member can be a single simple one piece construction which uses the inherent flexibility of the material and/or constructional structure rather than a complex arrangement of springs and diaphragms to bias the valve open by default and effect closure under increased pressure.

In the preferred embodiment, an aperture provided in a forward wall of the valve member is occluded by an essentially airtight contact with an inner surface of the forward wall of the valve housing. Therefore it follows that the forward aperture(s) are most conveniently provided in a side wall portion of the valve housing. Thus the valve housing conveniently comprises a forward wall, a rearward wall, and a forwardly extending side wall portion therebetween and the forward aperture(s) are provided in the forwardly extending side wall portion of the valve housing. In particular, a plurality of generally equally sized and shaped and generally equally spaced apertures are provided within the forwardly extending side wall portion of the valve housing. This ensures that pressure is distributed equally.

Such an arrangement offers particular advantages, since as air during normal breathing enters from the sides of the valve there is reduced chance of accidental occlusion by a garment or the like when compared with conventional prior art designs where the primary ingress during inhalation is located at the forward surface of the valve.

For convenience of construction, the valve housing preferably has a generally circular cross section, so as to define a generally cannular structure extending beyond the tracheostoma. The valve member therewithin preferably comprises a generally cylindrical sleeve, and in particular a generally cylindrical, concertina or bellows construction provided with an apertured forward wall. The forward wall preferably includes a single generally circular aperture so as to provide for a generally annular pressure surface on which the increased pressure associated with speech can act to effect expansion of the valve member in the manner above described.

The valve of the invention is adapted for fitment over the stoma of a laryngectomy patient to occlude the stoma during speech. It may be directly or indirectly adapted so to do. In the former case, the valve housing is provided with an integral rearwardly extending cannular portion adapted to be retained within the stoma of a tracheotomy patient to provide a breathing passage in use from the trachea of the patient to the valve.

In the latter case, the valve assembly as a whole is not designed to fit within the stoma, but rather a rear face of the rear wall is adapted for releasable engagement with a forward surface of a cannular device already so adapted for provision within the stoma of a patient. In this latter example, a valve in accordance with the invention may be provided for simple and releasable fitment to an existing cannulus within a stoma which might already have been provided for any conventional function, for example for cosmetic purposes, to protect the stoma, to keep external contaminants out of the trachea, to normalise heat-moisture conditions within the trachea, to control air flow resistance during normal breathing etc. This allows the valve to be readily removable for cleaning and replacement.

The valve aperture in the forward surface of the flexibly resilient valve member is preferably provided with a feathered edge. It is found that if a simple, full thickness edge is provided to this aperture, it exhibits a tendency to vibrate somewhat under speech pressures and effect a slightly imperfect air seal at the valve seating surface.

The tracheostoma valve preferably includes a "cough valve", that is a further aperture provided with a valve closure which is closed at both normal and speech breathing pressures, but which is caused to open under pressures higher than speech pressures. This deals with an emergency situation, in particular for example where the patient is coughing, to ensure that the tracheostoma valve is open when airway pressures are especially high.

In the preferred embodiment, wherein the valve member comprises a cylindrical sleeve for example in the manner of a bellows, with an apertured forward surface adapted to seat on a valve seating surface provided within the valve cavity on an inner surface of the valve housing in sealing manner as above described, and wherein the forward aperture(s) are provided within the forwardly extending side wall portion as above described, this further aperture is conveniently provided in the forward wall of the valve housing in the vicinity of the valve seat surface and is sealed by a cough valve closure openable at excessively high pressure to provide an emergency through passage.

In particular, the cough valve closure is a mushroom valve of suitably resilient material releasably retained within the said aperture such as to be blown open at high pressure. This is a particularly good safety feature, since it provides for a central, straight-line air flow path in an emergency situation and thus contrasts with prior art systems where the emergency path is indirect via a cough valve in the side of the cannular portion.

In a device in accordance with the invention the closure pressure necessary to effect closure of the valve member for speech is a consequence of the resilience of the valve member (both constructionally and materially), of the design of any surfaces thereof on which the air pressure acts, and of the degree of expansion which is necessary to effect closure against the valve seat portion of the valve housing. It is established in the art that characteristic vegetative and speech breathing pressures of patients can vary, both from patient to patient and in the same patient in different circumstances. Accordingly, it is generally desirable to provide the valve with means to adjust the pressure required to effect closure.

The present invention lends itself particularly well to this. The closure pressure can be adjusted quickly and simply merely by varying the length of the valve housing, so as to vary the distance between the rear wall where the valve member is anchored and the forward wall against which the valve member abuts to be occluded to effect closure of the valve.

In a preferred embodiment therefore, means are provided within the valve housing to adjust the length thereof, that is to adjust the distance between the rear wall and the forward wall. Preferably, these means are readily operable by the patient when the device is in situ. Conveniently, this is effected in that the valve housing is provided in at least two connected parts, one part including the rear wall and one part including the forward wall, together provided with a coupling which incorporates means to adjust the relative position of the two parts. Most conveniently, this comprises an adjustable screw thread connection, but alternative connections, such as telescoping connections or the like, will also be applicable.

In accordance with the invention it is thus possible to provide a tracheostoma valve with all of the features of the prior art devices, including automatic closure by speech breathing pressure, an ability for a patient to adjust the closure pressure, and provision of a cough valve for emergencies, which is of very simple construction, which is readily fabricated and which is readily removable for cleaning or replacement.

The valve housing or pieces thereof where applicable are preferably fabricated from relatively rigid material. In particular, the valve housing is fabricated from relatively rigid plastics material. A polyester is particularly preferred, but other relatively rigid materials such as polycarbonate, unplasticised vinyl polymers (for example rigid PVC) and the like are also likely to be applicable.

The valve member is preferably of inherently flexibly resilient material/construction, and in particular is fabricated from an elastomeric material. Suitable materials include natural or synthetic rubbers or other elastomeric plastics materials. Silicone rubbers (polysiloxanes) are particularly preferred.

Figure 2:
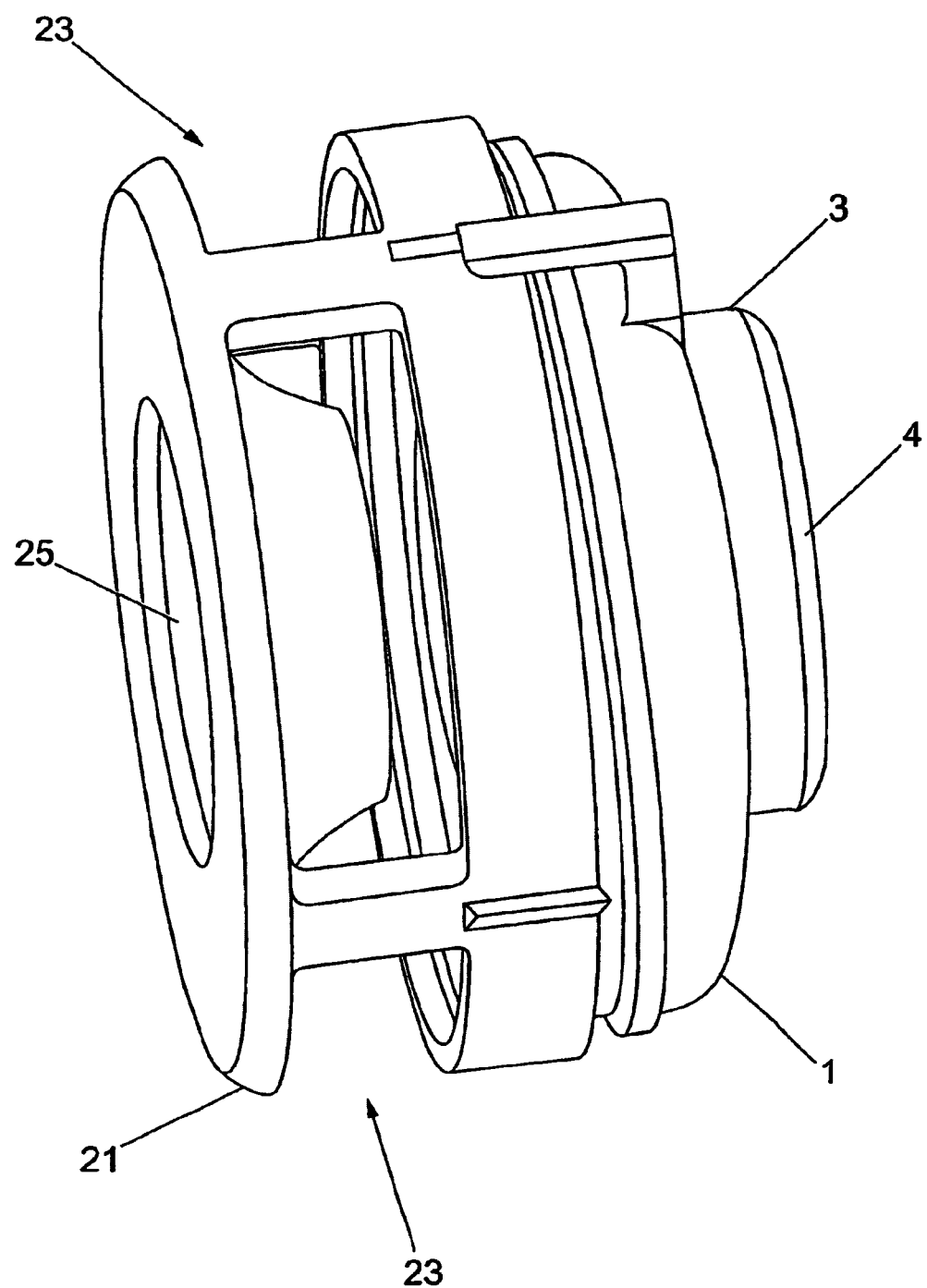
FIG. 2 is a perspective view of an embodiment of the invention looking generally from the side.
Figure 3:
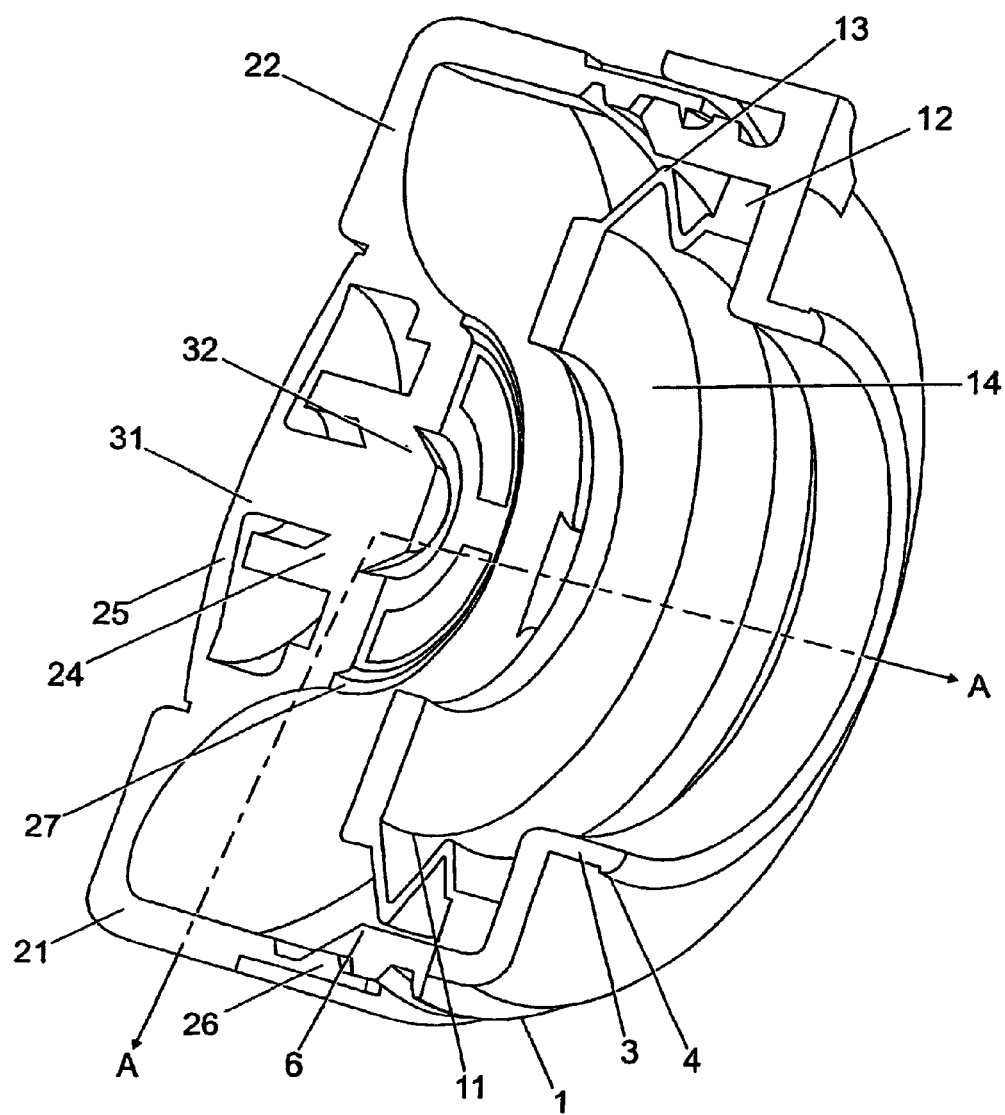
FIG. 3 is a partially cut away view of the embodiment of FIGS. 1 and 2 illustrating the valve cavity.

The invention will now be described by way of example only with reference to FIGS. 1 to 3 of the accompanying drawings.

Referring to the Figures, a simple four piece valve construction is illustrated. The housing is in two parts, consisting of a rear part (1) and a front part (21) both molded from polyester. The remaining components are the main valve, the bellows (11) and the cough valve, the mushroom valve (31), both fabricated from silicone.

The rear part (1) defines a circular aperture (2) opening into the chamber of the housing. A mounting portion is provided comprising a rear projection (3) having a lip (4) to facilitate releasable engagement of the valve housing with a suitably configured portion of the forward part of a cannular device already seated in the stoma of a patient. This device may, for example, serve as a filter in conventional manner, and is not material to the present invention.

The forward part of the housing (21) defines the main valve cavity (22) and is provided with apertures (23) disposed generally equidistantly around a laterally extending side wall thereon. This defines a normal air flow passage during normal vegetative breathing, when the valve member (11) is in the collapsed configuration as shown in FIG. 3, which is identified in the Figure by the arrows (A).

The forward part (21) includes a further aperture (25) into which is seated a silicone mushroom valve (31). This valve is retained by a barb (32) in interference fit with corresponding projecting portions (24) in the wall of the forward part (21). This interference fit is sufficient to retain the mushroom valve (31) in position not only when the main valve is fully open during normal breathing but also when the main valve is closed at the pressures normally associated with speech. However, at significantly higher pressures, such as might arise in a cough emergency, the mushroom valve (31) is blown open to provide for an emergency direct air flow passage directly through the centre of the valve.

The two parts (1, 21) of the valve housing are engaged together by means of the threaded portions (6, 26). The screw thread connection serves not only to hold the two halves together but also to allow for simple adjustment by a patient of the length of the housing, and thus in effect adjustment of the closure pressure required for speech.

In use during normal breathing air passes both ways in the direction (A) through the aperture provided in the bellows valve (11). The bellows valve is of inherently an astomeric resilient material, and is fixedly mounted to an inner wall of the housing by mounting portions (12). The bellows valve is provided with a concertina wall structure (13). The aperture in part of the forward wall of the bellows valve results in the presentation of a pressure surface (14) on which breathing pressure can act.

The extra pressure associated with speech, acting on the pressure surface (14), causes the concertina part of the bellows valve to expand, and the wall (14) is forced forward. At a particular pressure it has expanded sufficiently to come into contact with pressure surfaces (27) on an inner wall of the forward part (21). This effects closure of the valve. Air is no longer able to pass along the through route (A) and accordingly passes up the trachea of the patient through a suitable voice prosthesis to allow speech in the manner familiar.

This embodiment of the invention thus provides all of the functions required of a tracheostoma valve in admirable manner. Even providing for such optional features as a cough valve and a means to adjust the speech closure pressure, the embodiment illustrates that a device can be fabricated from only two materials and from only four components. The absence of complex mechanical moving parts leaves the valve simple in construction, less likely to break down, and particularly easy to clean. The valve is readily fixed to existing cannular devices such as HME stoma filters within the stoma of a patient and readily removable for cleaning or disposal.

The invention claimed is:

1. A tracheostoma valve comprising a valve housing defining a valve cavity and having at least one rearward and at least one forward aperture such as to define an air flow passage through the valve cavity between the rearward and forward apertures; and further comprising within the valve cavity a valve member deployable from a first collapsed configuration under vegetative breathing pressure wherein the air flow passage is open to a second expanded configuration under speech pressure whereat the valve member acts to restrict flow through the air flow passage, wherein the valve member comprises a rear portion fixedly mounted to an inner surface of the valve housing rearward of the forward aperture so as to surroundingly and sealingly engage over the rearward aperture, a forward portion, and a collapsibly expandable sleeve portion provided therebetween to surroundingly define a part of the air flow passage, such that the forward portion is deployable from a position in the unexpanded configuration whereat the air flow passage is open to a position in the expanded configuration whereat the forward portion acts to restrict air flow through the air flow passage; wherein:
the forward portion incorporates a valve aperture and a valve seating surface is provided within the valve cavity on an inner surface of the valve housing such that when the valve member is in the expanded configuration the forward portion of the valve member seats against the valve seating surface in sealing manner to effect closure of the valve aperture therein and hence generally occlude the air flow passage; and
the forward portion of the valve member comprises a partly apertured forward surface which forward surface is adapted to engage in fluid tight manner with the valve seating surface provided internally on the forward wall of the valve housing to effect closure of the air flow passage when the valve member is in the expanded configuration.

2. A tracheostoma valve in accordance with claim 1 wherein the sleeve portion is structured to facilitate expansion of the valve member in use.

3. A tracheostoma valve in accordance with claim 2 wherein the sleeve portion has a concertina structure.

4. A tracheostoma valve in accordance with claim 1 wherein the sleeve portion is resiliently biased to the unexpanded configuration.

5. A tracheostoma valve in accordance with claim 4 wherein the sleeve portion is fabricated from flexible material and biased to the unexpanded configuration by provision of separate biasing means.

6. A tracheostoma valve in accordance with claim 4 wherein the sleeve is fabricated from inherently resiliently expandable material, such as elastomeric material, and is so configured that the inherent resilience biases the valve member to the unexpanded configuration.

7. A tracheostoma valve in accordance with claim 1 wherein the aperture in the forward surface of the valve member is provided with a feathered edge.

8. A tracheostoma valve in accordance with claim 1 wherein the valve housing is provided with an integral rearwardly extending cannular portion adapted to be retained within the stoma of a tracheotomy patient to provide a breathing passage in use from the trachea of the patient to the valve, or a rear face of the housing is adapted for releasable engagement with a forward surface of a cannular device already so adapted for provision within the stoma of a patient.

9. A tracheostoma valve comprising a valve housing defining a valve cavity and having at least one rearward and at least one forward aperture such as to define an air flow passage through the valve cavity between the rearward and forward apertures; and further comprising within the valve cavity a valve member deployable from a first collapsed configuration under vegetative breathing pressure wherein the air flow passage is open to a second expanded configuration under speech pressure whereat the valve member acts to restrict flow through the air flow passage, wherein the valve member comprises a rear portion fixedly mounted to an inner surface of the valve housing rearward of the forward aperture so as to surroundingly and sealingly engage over the rearward aperture, a forward portion, and a collapsibly expandable sleeve portion provided therebetween to surroundingly define a part of the air flow passage, such that the forward portion is deployable from a position in the unexpanded configuration whereat the air flow passage is open to a position in the expanded configuration whereat the forward portion acts to restrict air flow through the air flow passage; wherein:
the valve housing comprises a forward wall, a rearward wall, and a forwardly extending side wall portion therebetween and the forward aperture(s) are provided in the forwardly extending side wall portion of the valve housing.

10. A tracheostoma valve in accordance with claim 9 wherein a plurality of generally equally sized and shaped and generally equally spaced apertures are provided within the forwardly extending side wall portion of the valve housing.

11. A tracheostoma valve comprising a valve housing defining a valve cavity and having at least one rearward and at least one forward aperture such as to define an air flow passage through the valve cavity between the rearward and forward apertures; and further comprising within the valve cavity a valve member deployable from a first collapsed configuration under vegetative breathing pressure wherein the air flow passage is open to a second expanded configuration under speech pressure whereat the valve member acts to restrict flow through the air flow passage, wherein the valve member comprises a rear portion fixedly mounted to an inner surface of the valve housing rearward of the forward aperture so as to surroundingly and sealingly engage over the rearward aperture, a forward portion, and a collapsibly expandable sleeve portion provided therebetween to surroundingly define a part of the air flow passage, such that the forward portion is deployable from a position in the unexpanded configuration whereat the air flow passage is open to a position in the expanded configuration whereat the forward portion acts to restrict air flow through the air flow passage; wherein:
the tracheostoma valve further comprises an additional aperture provided with a valve closure which is closed at both normal and speech breathing pressures, but which is caused to open under pressures higher than speech pressures.

12. A tracheostoma valve in accordance with claim 11, wherein the valve member comprises a sleeve portion with an apertured forward surface adapted to seat on a valve seating surface provided within the valve cavity on an inner surface of the valve housing in sealing manner; and wherein the valve housing comprises a forward wall, a rearward wall, and a forwardly extending side wall portion therebetween and the forward aperture(s) are provided in the forwardly extending side wall portion of the valve housing; and wherein this additional aperture is provided in the forward wall of the valve housing in the vicinity of the valve seating surface and is sealed by a cough valve closure openable at excessively high pressure to provide an emergency through passage.

13. A tracheostoma valve in accordance with claim 12 wherein the cough valve closure is a mushroom valve of suitably resilient material releasably retained within the aperture such as to be blown open at high pressure.

14. A tracheostoma valve in accordance with claim 13 wherein the valve housing is provided in at least two connected parts, one part including a rear wall and one part including a forward wall, together provided with a coupling which incorporates means to adjust the relative position of the two parts.

15. A tracheostoma valve comprising a valve housing defining a valve cavity and having at least one rearward and at least one forward aperture such as to define an air flow passage through the valve cavity between the rearward and forward apertures; and further comprising within the valve cavity a valve member deployable from a first collapsed configuration under vegetative breathing pressure wherein the air flow passage is open to a second expanded configuration under speech pressure whereat the valve member acts to restrict flow through the air flow passage, wherein the valve member comprises a rear portion fixedly mounted to an inner surface of the valve housing rearward of the forward aperture so as to surroundingly and sealingly engage over the rearward aperture, a forward portion, and a collapsibly expandable sleeve portion provided therebetween to surroundingly define a part of the air flow passage, such that the forward portion is deployable from a position in the unexpanded configuration whereat the air flow passage is open to a position in the expanded configuration whereat the forward portion acts to restrict air flow through the air flow passage; wherein:

means are provided within the valve housing to adjust the length thereof.

* * * * *